United States Patent
Tsai et al.

(10) Patent No.: US 9,603,867 B2
(45) Date of Patent: Mar. 28, 2017

(54) PHARMACEUTICAL COMPOSITION FOR IMPROVING WOUND HEALING OR PROPHYLACTICALLY PREVENTING OR INHIBITING SCAR FORMATION

(71) Applicant: YUNG SHIN PHARM. IND. CO., LTD., Taichung (TW)

(72) Inventors: Chiung-Ju Tsai, Miaoli County (TW); Yen-Ling Yi, Taichung (TW); Man-Hsin Wang, Taichung (TW); Shih-Lung Chang, Taichung (TW); Chia-Chun Lee, Nantou County (TW)

(73) Assignee: YUNG SHIN PHARM. IND. CO., LTD., Taichung (TW)

( * ) Notice: Subject to any disclaimer, the term of this patent is extended or adjusted under 35 U.S.C. 154(b) by 64 days.

(21) Appl. No.: 14/637,364

(22) Filed: Mar. 3, 2015

(65) Prior Publication Data

US 2016/0256482 A1    Sep. 8, 2016

(51) Int. Cl.
| | | |
|---|---|---|
| *A61K 31/07* | (2006.01) | |
| *A61K 31/355* | (2006.01) | |
| *A61K 31/59* | (2006.01) | |
| *A61K 31/728* | (2006.01) | |
| *A61K 31/19* | (2006.01) | |
| *A61K 31/197* | (2006.01) | |
| *A61K 31/593* | (2006.01) | |
| *A61K 9/00* | (2006.01) | |
| *A61K 47/10* | (2017.01) | |
| *A61K 9/06* | (2006.01) | |

(52) U.S. Cl.
CPC .......... *A61K 31/728* (2013.01); *A61K 9/0014* (2013.01); *A61K 9/06* (2013.01); *A61K 31/07* (2013.01); *A61K 31/19* (2013.01); *A61K 31/197* (2013.01); *A61K 31/355* (2013.01); *A61K 31/593* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 4,736,024 A * | 4/1988 | Della Valle | A61K 9/0048 536/101 |
| 8,835,405 B2 | 9/2014 | Lin | |
| 2013/0072452 A1* | 3/2013 | Lin | A61K 9/0019 514/54 |

FOREIGN PATENT DOCUMENTS

| | | |
|---|---|---|
| CN | 1285193 A | 2/2001 |
| CN | 102357258 A | 2/2012 |
| TW | 201313236 A1 | 4/2013 |

OTHER PUBLICATIONS

Now Foods, Liquid Hyaluronic Acid Joint Support product, http://www.nutritionexpress.com/now+foods/supplements/now+foods+liquid+hyaluronic+acid+Go, Aug. 28, 2013, obtained from the internet archive.*
Yong, CN 103191042 A, Jul. 10, 2013, machine translation.*
Vitamin E Fact Sheet, National Institutes of Health, downloaded from the internet Aug. 31, 2016.*
Fan Yan-yan et al., Activation of α7nAChR promotes wound healing in diabetic mice by suppressing TNF-α expression, Chinese Journal of Pathophysiology, 2013, 29(6), pp. 1053-1058, vol. 29, Issue 6.

* cited by examiner

*Primary Examiner* — Layla Berry
(74) *Attorney, Agent, or Firm* — Winston Hsu; Scott Margo

(57) ABSTRACT

A pharmaceutical composition for improving wound healing is provided. The pharmaceutical composition includes (a) hyaluronic acid or its derivation, (b) an effective amount of an active ingredient; and optionally (c) pharmaceutically acceptable carriers and/or excipients. In one embodiment, the active ingredient includes vitamin. In another embodiment, the active ingredient includes acexamic acid. In still another embodiment, the pharmaceutical composition can further comprise sorbic acid.

12 Claims, 4 Drawing Sheets

PHARMACEUTICAL COMPOSITION FOR IMPROVING WOUND HEALING OR PROPHYLACTICALLY PREVENTING OR INHIBITING SCAR FORMATION

BACKGROUND OF THE INVENTION

1. Field of the Invention

The present invention is related to a pharmaceutical composition, and more particularly, to a pharmaceutical composition for improving wound healing or prophylactically preventing or inhibiting scar formation on wound region.

2. Description of the Prior Art

Wounds, such as burns, frostbite, stab, incisor wounds and other trauma, or pain associated with infection after surgery, inevitably occur in the daily lift. The more delay of wound healing, the more difficult will scars disappear after wounds healing. It is an important issue to shorten the wound healing time and preventing scarring.

Wound healing process can simply be divided into three stages, namely inflammation phase, proliferative phase and tissue remodel phase. The scar is an inevitable result during the repairing process in wound region to healing. After the normal wound healing, blood vessels in original site of the wound region will gradually become atrophied, and collagen in such site will re-construct and development, thereby forming scars. In the 3-6 months after injury, scarring tissue exhibits the strongest activity and is most difficult to eliminate. As a result, it is believed that preventing scar formation is more important than eliminating it. Providing a good healing condition at the first beginning would improve wound healing, as well as preventing or decreasing the possibility of scarring.

It is known that wound healing and scaring may be affected by many factors, including gene, degrees of injury, type of injured organ and location, techniques of surgical suture, degrees of infection, the personal physical fitness and body case, the care of the wound after surgery, nutritional supplements or immunity condition. Evidence shows that when the wound is infectious or other foreign matter is not completely removed from the injured site, scarring or tissue necrosis would occur and wound healing will be delayed. In some situation, hypertrophic scars will be formed, which is known as keloid.

Conventionally, artificial leather or silicon-containing medical material is used in wound healing to prevent or reduce scarring. However, it is disadvantageous when using such artificial leather since it has restrictions such as: not suitable for tissue or wounds that are over fluid oozing, the wounds that expose bones and muscles, wounds surrounded with fragile tissue, the deep wounds or the wounds that may leak in a lower edge. Otherwise, the artificial leather makes the wound region difficult to observe, and it also costs a lot in general daily care. Moreover, comparing to the artificial leather, silicon-containing film costs much higher and also has the shortcomings of poor permeability, and only physical therapy effect can be provided.

SUMMARY OF THE INVENTION

According to one embodiment, a pharmaceutical composition for improving wound healing is provided or prophylactically preventing or inhibiting scar formation on wound region. The pharmaceutical composition includes (a) hyaluronic acid or its derivation, (b) an effective amount of an active ingredient; and optionally (c) pharmaceutically acceptable carriers and/or excipients. In one embodiment, the active ingredient includes vitamin. In another embodiment, the active ingredient includes acexamic acid. In still another embodiment, the pharmaceutical composition can further comprise sorbic acid.

The pharmaceutical composition provided by the present invention can not only help wound healing and reduce the healing time, but also can reduce the possibility of scar forming.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

FIG. 3 and FIG. 4 show bar charts of evaluation of wound healing in vivo models, wherein FIG. 3 shows the incision wound model and FIG. 4 shows the burn wound model.

DETAILED DESCRIPTION

Figure 1:
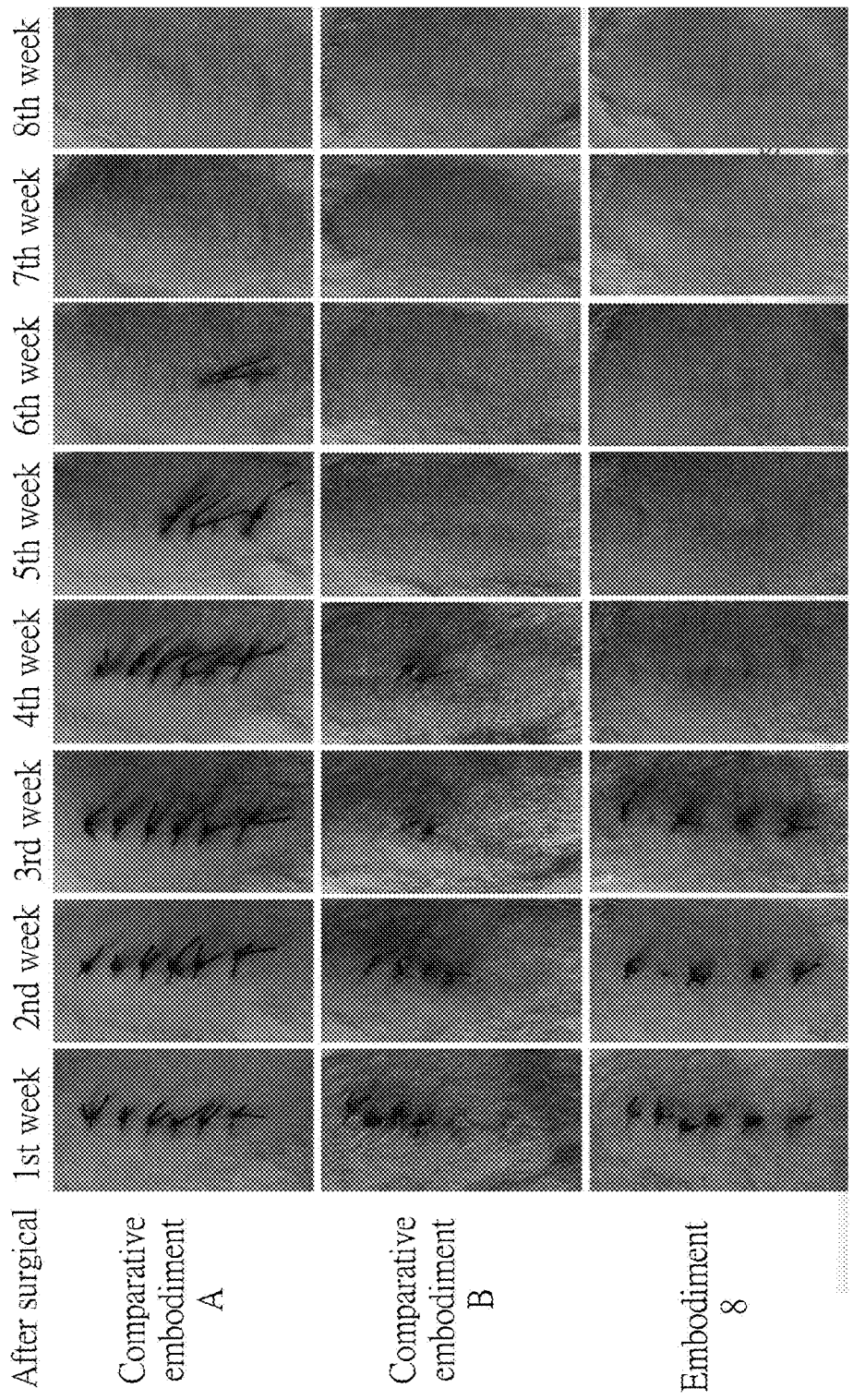
FIG. 1 shows pictures of surgical suture wound of animals after administrating the composition of comparative embodiment A, comparative embodiment B and embodiment 8, respectively.

To provide a better understanding of the presented invention, preferred embodiments will be made in detail. The preferred embodiments of the present invention are illustrated in the accompanying drawings with numbered elements.

The present invention is directed to a pharmaceutical composition with hyaluronic acid that can improve wound healing, shortening healing time, prophylactically preventing or inhibiting scar formation on wound region. The pharmaceutical composition includes (a) hyaluronic acid or its derivation, (b) an effective amount of an active ingredient; and optionally (c) pharmaceutically acceptable carriers and/or excipients.

Regarding to hyaluronic acid, it is also known as uronic acid, hyaluronic acid, hyaluronic acid, etc., and the basic structure is composed of disaccharide units D-glucuronic acid and N-acetyl glucosamine for example. It differs from other mucopolysaccharides by containing no sulfur. In one embodiment, the derivation of said hydrofluoric acid can be any form of salts, such as sodium salts. In one embodiment, said hyaluronic acid or its derivation refers to a low molecular weight hyaluronic acid, such as hyaluronic acid having a molecular weight lower than 1000 kDa, preferably between 200 kDa and 1000 kDa, more preferably between 200 kDa and 400 kDa. In one embodiment, a concentration of the hyaluronic acid or its derivation is substantially between 0.005 and 20% w/w (or w/v), preferably between 0.01 and 10% w/w (or w/v).

A concentration of said effective amount of the active ingredient may substantially between 0.0130% w/w for example. In one embodiment, said active ingredient includes a vitamin, such as vitamin A, vitamin D, vitamin E, their derivations, or combinations thereof. In one embodiment, a concentration of vitamin A is 100-40000 IU/g, preferably 200-20000 IU/g, most preferably 200-3000 IU/g. In one preferred embodiment, a concentration of vitamin D is 20-10000 IU/g, preferably 50-5000 IU/g, most preferably 50-600 IU/g. In one preferred embodiment, a concentration of vitamin E (Tocopherol for example) is 0.001-20% w/w (or w/v), preferably 0.01-10% w/w (or w/v), most preferably 0.002-5% w/w (or w/v). In another embodiment, the active ingredient includes acexamic acid (N-acetyl-amino-6-hexanoic acid) or its deviation, with a concentration of 0.5-20% w/w (or w/v), preferably 1-10% w/w (w/v). It is noted that the above-mentioned various active ingredient can be incorporated with the hyaluronic acid singly or multiply. For instance, the pharmaceutical composition in one embodiment can include a hyaluronic acid, and a vitamin consisted of vitamin A, vitamin D and vitamin E. In another embodiment, the pharmaceutical composition includes a hyaluronic acid, and a vitamin consisted of vitamin A and vitamin D. In another embodiment, the pharmaceutical composition includes a hyaluronic acid, a vitamin consisted of vitamin A and vitamin D, and acexamic acid. In another embodiment, besides the active ingredient, the pharmaceutical composition can further include sorbic acid with a concentration of 0.1-1% (w/w), thereby improving the anti-infection or anti-fungi ability. In one preferred embodiment, the sorbic acid is in combination with acexamic acid and hyaluronic acid.

In one embodiment, the pharmaceutically acceptable carriers and/or excipients refer to any composition that can be applied to human security without having the effect of a particular ingredient. The pharmaceutical composition can be made of any medical form when filling, transportation or using, such as solution, gel, emugel, cream, ointment, lotion, transdermal system, suspension or patch, and is not limited thereto. Preferably, the pharmaceutical composition is formed of emugel, cream, or transdermal system. More preferably, it is formed of emugel. In another embodiment, the pharmaceutical composition can be a dressing material attached on a substrate such that the wound tissue with fibroblasts can be directly or indirectly exposed to the pharmaceutical composition. The fibroblasts in not limited to skin tissue but can be other tissue inside the injured individual. For example, the substrate with dressing material having the pharmaceutical composition can be a biological duct, stent, or pacemaker, but is not limited thereto. Moreover, the term "individual" in the present invention represents to an animal, in particularly mammalian (such as an ape, cattle, horse, sheep, rodent, goat, dog, cat, rabbit), preferably human.

Said pharmaceutical compositions including hyaluronic acid and the active ingredients can help wound healing and can be applied to any wound regions, such as trauma, surgery part, vascular osteitis, ulcerative varicose veins, arterial ulcers, pressure ulcers or other wounds ulcerative scars, burns and is not limited thereto. It is surprising found that the pharmaceutical compositions not only can improve wound healing but also can prophylactically prevent or inhibiting scar formation during wound healing.

Specifically, the present invention relates to a pharmaceutical composition in wound caring, comprising hyaluronic acid or a derivative thereof. In one embodiment, the pharmaceutical composition further comprises a vitamin, such as vitamin A (for example, 200-20000 IU/g), vitamin D (for example, 50-5000 IU/g) or vitamin E (such as Tocopherol 0.01%-10% 2/2), singly or their combination. The pharmaceutical composition can improve wound healing. Also, it can prophylactically prevent or inhibit scar formation on wound region. Through clinical experiments, it is found that by using the pharmaceutical composition, the healing time of the injured tissue is shortened, and less or no scar is produced by comparing other comparative embodiments.

In another embodiment, the pharmaceutical composition with hyaluronic acid can be in combination with acexamic acid (epsilon-acetamidocaproic) (1-10%) for improving the wound healing ability or decreasing scarring in wounded region. It is found that the after administrating the pharmaceutical composition containing hyaluronic acid in combination with acexamic acid, good wound healing is observed and the wound region becomes more flat, in comparing with other embodiments using only hyaluronic acid or acexamic acid. From the observation of in vivo wound healing experiment, it is shown that the pharmaceutical composition with hyaluronic acid in combination of acexamic acid can enhance cell proliferation, facilitate the recovery of injured region or tissue, as well as shortening the scarring time or preventing the scarring scab, exhibiting unexpected results and superior effect in wound healing and inhibiting scar formation.

In one embodiment, the pharmaceutical composition having hyaluronic acid (or its derivative) can further include sorbic acid. Sorbic acid added in the pharmaceutical composition can upgrade the disinfectant and anti-fungal effect, so as to improve the cleanness of ulcers region or other infectious region caused by fungal for example. It is noted that the pharmaceutical composition in this embodiment is suitable for the oppression medical materials or supplies, such as cosmetic tape, patch, thin film, protective film, but is not limited thereto. As such, the wound region with scarring is subjected to hypoxia environment, the proliferation rate thereof is reduced and scar formation can be reduced or avoided. For instance, when a damage has been formed in dermis, initial proper wound treatment and care by using the composition of the present invention can reduce the chances of scar deterioration, and wound care in the late with pharmaceutical compositions of the present invention is applied to a variety of scar treatment. Consequently, it can effectively reduce or eliminate the scars.

Embodiment 1

| | Ingredient | Concentration |
|---|---|---|
| 1 | Vitamin A | 200,000 IU |
| 2 | Vitamin D | 50,000 IU |
| 3 | Vitamin E | 0.2 g |
| 4 | Hyaluronic acid (sodium salt) | 0.2 g |
| 5 | Propylene Glycol | 20 g |
| 6 | Triethanolamine | 2 g |
| 7 | Carboxypolymethylene | 1 g |
| 8 | Cetyl alcohol | 1 g |
| 9 | Tween 60 | 4 g |
| 10 | Span 60 | 6 g |
| 11 | Stearyl alcohol | 3 g |
| 12 | Purified water | Add. to 100 g |

In this embodiment, the pharmaceutical composition is prepared by:

(a) mixing (7) and (12) and stirring until completely dissolved, followed by adding (5) and (6) continue stirring until evenly;

(b) mixing (8), (10) and (11), heated to about 75° C., then stirring until completely dissolved;

(c) mixing (9) and (12) and heated to 75° C., then stirring until completely dissolved; next, adding it into the mixture of (b) and emulsifying mixing for 10 minutes by a homo-mixer;

(d) cooling the product of (c) to 40° C. and adding the mixture of (a), the compounds (1), (2), (3) and (4), stirring till evening, and fill into a container under room temperature.

| Embodiment 2 | | | |
|---|---|---|---|
| | Ingredient | Concentration | |
| 1 | Vitamin A | 200,000 | IU |
| 2 | Vitamin D | 50,000 | IU |
| 3 | Vitamin E | 0.02 | g |
| 4 | Hyaluronic acid (sodium salt) | 0.2 | g |
| 5 | Propylene Glycol | 20 | g |
| 6 | Triethanolamine | 2 | g |
| 7 | Carboxypolymethylene | 1 | g |
| 8 | Cetyl alcohol | 1 | g |
| 9 | Tween 60 | 4 | g |
| 10 | Span 60 | 6 | g |
| 11 | Stearyl alcohol | 3 | g |
| 12 | Purified water | Add. to 100 | g |

In this embodiment, the pharmaceutical composition is prepared by:

(a) mixing (7) and (12) and stirring until completely dissolved, followed by adding (5) and (6) continue stirring until evenly;

(b) mixing (8), (10) and (11), heated to about 75 t, then stirring until completely dissolved;

(c) mixing (9) and (12) and heated to 75° C., then stirring until completely dissolved; next, adding it into the mixture of (b) and emulsifying mixing for 10 minutes by a homomixer;

(d) cooling the product of (c) to 40° C. and adding the mixture of (a), the compounds (1), (2), (3) and (4), stirring till evening, and fill into a container under room temperature.

| Embodiment 3 | | | |
|---|---|---|---|
| | Ingredient | Concentration | |
| 1 | Vitamin A | 200,000 | IU |
| 2 | Vitamin D | 50,000 | IU |
| 3 | Vitamin E | 0.02 | g |
| 4 | Hyaluronic acid (sodium salt) | 3 | g |
| 5 | Propylene Glycol | 20 | g |
| 6 | Cetyl alcohol | 1 | g |
| 7 | Tween 60 | 4 | g |
| 8 | Span 60 | 6 | g |
| 9 | Stearyl alcohol | 3 | g |
| 10 | Purified water | Add. to 100 | g |

In this embodiment, the pharmaceutical composition is prepared by:

(a) mixing (4) and appropriate amount of (10) and stirring them until completely dissolved;

(b) mixing (6), (8) and (9), heated to about 75° C., then stirring until completely dissolved;

(c) mixing (5), (7) and appropriate amount of (10) and heated to 75° C., then stirring until completely dissolved; adding into the mixture of (b) and emulsifying mixing 10 minutes by a homomixer;

(d) cooling the product of (c) to 40° C. and adding the mixture of (a), the compounds (1), (2), and (3), stirring till evening, and fill into a container under room temperature.

| Embodiment 4 | | | |
|---|---|---|---|
| 1 | Vitamin A | 100,000 | IU |
| 2 | Vitamin E | 0.02 | g |
| 3 | Hyaluronic acid (sodium salt) | 0.2 | g |
| 4 | Propylene Glycol | 20 | g |
| 5 | Cetyl alcohol | 1 | g |
| 6 | Tween 60 | 4 | g |
| 7 | Span 60 | 6 | g |
| 8 | Stearyl alcohol | 3 | g |
| 9 | Purified water | Add. to 100 | g |

In this embodiment, the pharmaceutical composition is prepared by:

(a) mixing (3), (4) and appropriate amount of (9) and stirring them until completely dissolved;

(b) mixing (6) and appropriate amount of (9), heated to about 75° C., then stirring until completely dissolved;

(c) mixing (5), (7) and (8) and heated to 75° C., then stirring until completely dissolved; adding it into the mixture of (b) and emulsifying mixing for 10 minutes by a homomixer;

(d) cooling the product of (c) to 40° C. and adding the mixture of (a), the compounds (1) and (2), stirring till evening, and fill into a container under room temperature.

| Embodiment 5 | | | |
|---|---|---|---|
| | Ingredient | Concentration | |
| 1 | Vitamin A | 100,000 | IU |
| 2 | Vitamin E | 0.02 | g |
| 3 | Hyaluronic acid (sodium salt) | 3 | g |
| 4 | Propylene Glycol | 20 | g |
| 5 | Cetyl alcohol | 1 | g |
| 6 | Tween 60 | 4 | g |
| 7 | Span 60 | 6 | g |
| 8 | Stearyl alcohol | 3 | g |
| 9 | Purified water | Add. to 100 | g |

In this embodiment, the pharmaceutical composition is prepared by:

(a) mixing (3), (4) and appropriate amount of (9) and stirring them until completely dissolved;

(b) mixing (6) and appropriate amount of (9), heated to about 75° C., then stirring until completely dissolved;

(c) mixing (5), (7) and (8) and heated to 75° C., then stirring until completely dissolved; adding it into the mixture of (b) and emulsifying mixing for 10 minutes by a homomixer;

(d) cooling the product of (c) to 40° C. and adding the mixture of (a), the compounds (1) and (2), stirring till evening, and fill into a container under room temperature.

| Embodiment 6 | | | |
|---|---|---|---|
| | Ingredient | Concentration | |
| 1 | Acexamic acid | 5 | g |
| 2 | Sorbic acid | 0.2 | g |
| 3 | Hyaluronic acid (sodium salt) | 1 | g |
| 4 | Propylene Glycol | 20 | g |
| 5 | Cetyl alcohol | 1 | g |
| 6 | Tween 60 | 4 | g |
| 7 | Span 60 | 6 | g |
| 8 | Stearyl alcohol | 3 | g |
| 9 | Purified water | Add. to 100 | g |

In this embodiment, the pharmaceutical composition is prepared by:

(a) mixing (1), (4), (6) and appropriate amount of (9) and stirring them until completely dissolved;

(b) mixing (5), (7) and (8), heated to about 75° C., then stirring until completely dissolved;

(c) mixing the product of (a) and the product of (b) into a homomixer and emulsifying mixing for 20 minutes;

(d) cooling the product of (c) to 40° C. and adding the compounds (2) and (3), stirring till evening, and fill into a container under room temperature.

Embodiment 7

| | Ingredient | Concentration |
|---|---|---|
| 1 | Acexamic acid | 10 g |
| 2 | Sorbic acid | 0.2 g |
| 3 | Hyaluronic acid (sodium salt) | 2 g |
| 4 | Propylene Glycol | 20 g |
| 5 | Cetyl alcohol | 1 g |
| 6 | Tween 60 | 4 g |
| 7 | Span 60 | 6 g |
| 8 | Stearyl alcohol | 3 g |
| 9 | Purified water | Add to 100 g |

In this embodiment, the pharmaceutical composition is prepared by:

(a) mixing (1), (4), (6) and (9), heated to about 75° C. and stirring them until completely dissolved;

(b) mixing (5), (7) and (8), then stirring until completely dissolved;

(c) mixing the product of (a) and the product of (b) into a homomixer and emulsifying mixing for 20 minutes;

(d) cooling the product of (c) to 40° C. and adding the compounds (2) and (3), stirring till evening, and fill into a container under room temperature.

TABLE 1

Embodiment 8

| | Comparative Embodiment A | Comparative Embodiment B | Embodiment 8 |
|---|---|---|---|
| Composition | Hyaluronic acid (0.2% w/w) | Vitamin A (200-3000 IU/g) Vitamin D (50-600 IU/g) Vitamin E (0.002-0.5% w/w) | Vitamin A (200-3000 IU/g) Vitamin D (50-600 IU/g) Vitamin E (0.002-0.5% w/w) Hyaluronic acid (0.1-0.5% w/w) |

Please refer to FIG. 1, showing pictures of surgical suture wound of animals after administrating the composition of comparative embodiment A, comparative embodiment B and embodiment 8. As shown in FIG. 1, it is shown that in comparative embodiment A, the surgical suture remains on the wound region till the sixth week after the surgery, while in comparative embodiment B, the surgical suture can still be seen in the fourth week after surgery. In comparison, the surgical suture in embodiment 8 remains only in the third week and disappears in the fourth week after surgery, showing superior would healing ability than comparative embodiment A and comparative embodiment B.

Figure 2:
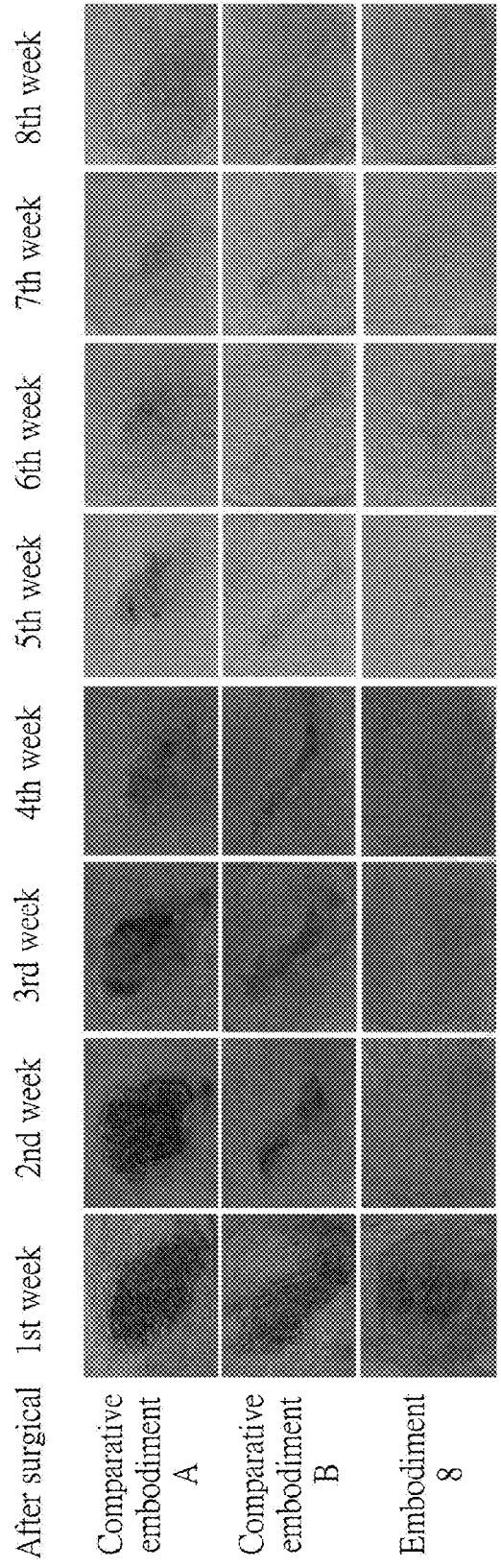
FIG. 2 shows pictures of burns region of animals after administrating the composition of comparative embodiment A, comparative embodiment B and embodiment 8, respectively.

Please refer to FIG. 2, showing pictures of burns region of animals after administrating the composition of comparative embodiment A, comparative embodiment B and embodiment 8. As shown in the figure, the burn wound region after applying the composition of embodiment 8 can significantly improve wound healing in comparing to the comparative embodiment A and comparative embodiment B. It is noted that nearly no scarring occurred in the embodiment 8 while there is scar even after wound healing in the comparative embodiment A and B. It is observed that the pharmaceutical composition with hyaluronic acid and vitamin can not only improve wound healing but also can inhibit scar formation.

Figure 3:
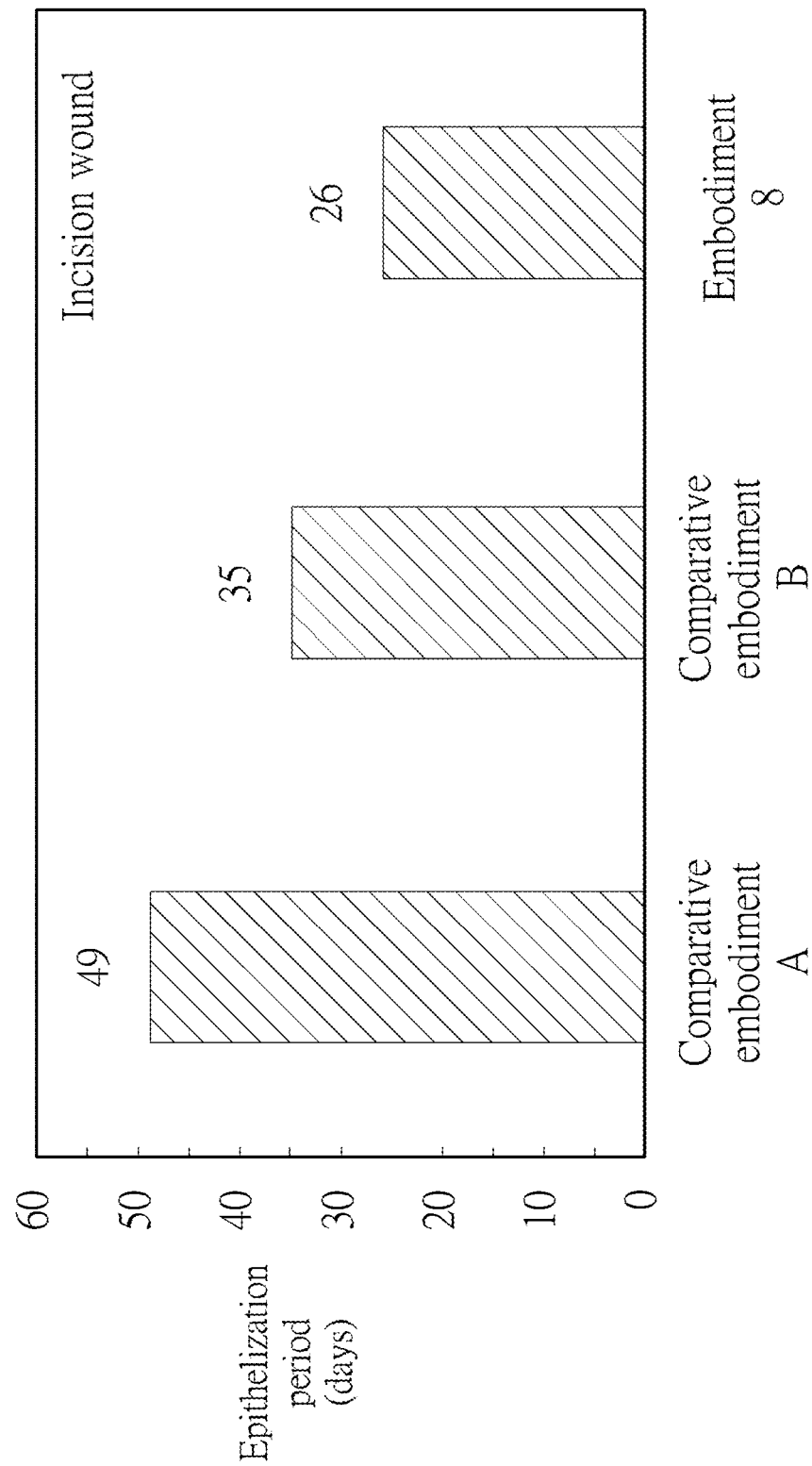
Figure 4:
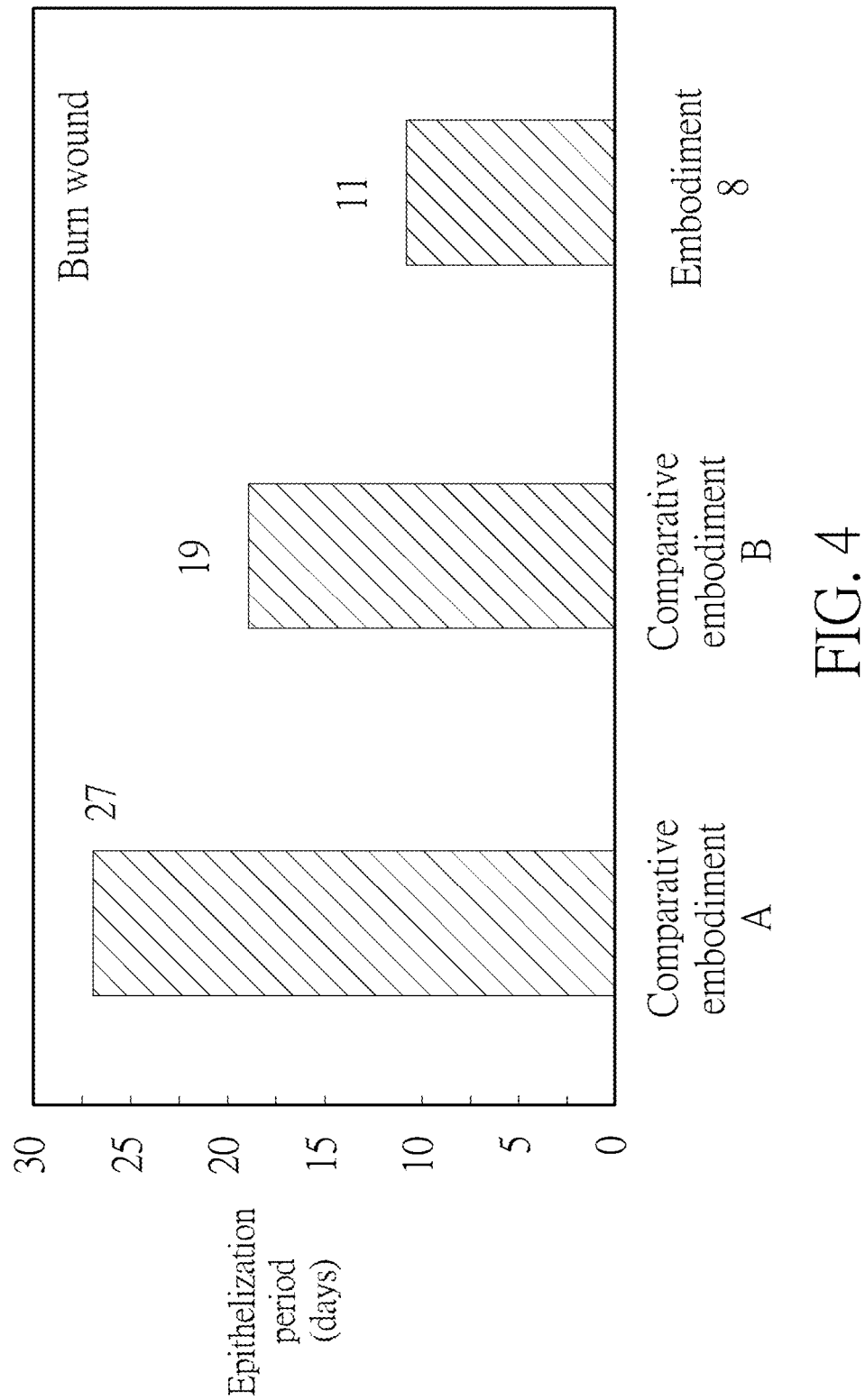

Please refer to FIG. 3 and FIG. 4, showing bar charts of evaluation of wound healing in vivo models, wherein FIG. 3 shows the incision wound model and FIG. 4 shows the burn wound model. As shown in FIG. 3, it takes about 49 weeks to heal the wound when applying the composition of comparative embodiment A, about 35 weeks when applying the composition of comparative embodiment B. However, it takes only 26 weeks when applying the composition of embodiment 8, significantly shortening the healing time. Regarding to the wound healing of burn wound, it takes about 27 weeks to heal the wound when applying the composition of comparative embodiment A, about 19 weeks when applying the composition of comparative embodiment B. Nevertheless, it takes only 11 weeks when applying the composition of embodiment 8.

From the above experiments, comparing to the comparative embodiment A with only hyaluronic acid, the comparative embodiment B with only vitamins, the embodiment of the present invention including hyaluronic acid in combination of vitamins can not only help wound healing and reduce the healing time, but also can reduce the possibility of scar forming. The pharmaceutical composition combining hyaluronic acid and vitamin therefore brings unexpected results in wound healing and therefore is suitable to be used in any wound region for clinical or cosmetically wound caring for example.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A pharmaceutical composition for improving wound healing, comprising a hyaluronic acid or a derivative thereof, and a vitamin, wherein the vitamin is consisted of 200-3000 IU/g vitamin A, 50-5000 IU/g vitamin D and 0.001-20% w/w vitamin E.

2. The pharmaceutical composition according to claim 1, wherein the hyaluronic acid is a low molecular weight hyaluronic acid, and the low molecular weight hyaluronic acid has a molecular weight between 200 kDa and 1000 kDa.

3. The pharmaceutical composition according to claim 2, wherein the low molecular weight hyaluronic acid has a molecular weight between 200 kDa and 400 kDa.

4. The pharmaceutical composition according to claim 1, wherein the pharmaceutical composition is formed of solution, gel, emulsion, cream, ointment, lotion, transdermal system, suspension or patch.

5. The pharmaceutical composition according to claim 1, wherein the pharmaceutical composition is formed of emulsion, cream, or transdermal system.

6. The pharmaceutical composition according to claim 1, wherein the pharmaceutical composition is formed of emulsion.

7. A pharmaceutical composition for prophylactically preventing or inhibiting scar formation on wound region, comprising a hyaluronic acid or a derivative thereof, and a vitamin, wherein the vitamin is consisted of 200-3000 IU/g vitamin A, 50-5000 IU/g vitamin D and 0.001-20% w/w vitamin E.

8. The pharmaceutical composition according to claim 7, wherein the hyaluronic acid is a low molecular weight hyaluronic acid, and the low molecular weight hyaluronic acid has a molecular weight between 200 kDa and 1000 kDa.

9. The pharmaceutical composition according to claim 8, wherein the low molecular weight hyaluronic acid has a molecular weight between 200 kDa and 400 kDa.

10. The pharmaceutical composition according to claim 7, wherein the pharmaceutical composition is formed of solution, gel, emulsion, cream, ointment, lotion, transdermal system, suspension or patch.

11. The pharmaceutical composition according to claim 7, wherein the pharmaceutical composition is formed of emulsion, cream, or transdermal system.

12. The pharmaceutical composition according to claim 7, wherein the pharmaceutical composition is formed of emulsion.

\* \* \* \* \*